United States Patent
Meinzinger et al.

(10) Patent No.: US 9,155,807 B2
(45) Date of Patent: Oct. 13, 2015

(54) METHOD AND APPARATUS FOR THE STERILIZATION OF CONTAINERS

(75) Inventors: Rupert Meinzinger, Kirchroth (DE); Johann Justl, Regensburg (DE)

(73) Assignee: Krones AG, Neutraubling (DE)

(*) Notice: Subject to any disclaimer, the term of this patent is extended or adjusted under 35 U.S.C. 154(b) by 0 days.

(21) Appl. No.: 13/397,946

(22) Filed: Feb. 16, 2012

(65) Prior Publication Data

US 2012/0219455 A1    Aug. 30, 2012

(30) Foreign Application Priority Data

Feb. 24, 2011    (DE) .................... 10 2011 012 342

(51) Int. Cl.
*A61L 2/08*    (2006.01)
*B65B 55/08*    (2006.01)

(52) U.S. Cl.
CPC ............... *A61L 2/087* (2013.01); *B65B 55/08* (2013.01); *A61L 2202/23* (2013.01)

(58) Field of Classification Search
CPC ...................................... A61L 2/087
USPC ............................................ 422/22
See application file for complete search history.

(56) References Cited

U.S. PATENT DOCUMENTS

| | | | |
|---|---|---|---|
| 2011/0012030 A1* | 1/2011 | Bufano | A61L 2/087 250/492.3 |
| 2011/0012032 A1* | 1/2011 | Bufano et al. | 250/492.3 |

FOREIGN PATENT DOCUMENTS

| | | |
|---|---|---|
| DE | 10 2008 007 428 | 8/2009 |
| DE | 10 2008 045 187 | 3/2010 |
| DE | 10 2009 008633 | 8/2010 |
| EP | 2161202 | 3/2010 |
| EP | 2371397 | 10/2011 |
| WO | 2009/095182 | 8/2009 |
| WO | 2011/067393 | 6/2011 |
| WO | 2011/080245 | 7/2011 |

* cited by examiner

*Primary Examiner* — Sean E Conley
*Assistant Examiner* — Donald Spamer
(74) *Attorney, Agent, or Firm* — Greer, Burns & Crain, Ltd.

(57) ABSTRACT

A method of sterilizing containers, wherein the containers are conveyed along a pre-set conveying path by a conveying device, and wherein an irradiation device is introduced by a relative movement between the container and the irradiation device in a longitudinal direction of the container into the interior of the container to be sterilized and emits a charge carrier irradiation to sterilize the inner wall of the container by the charge carrier irradiation, wherein an aperture region situated on the outside of the container is also sterilized.

21 Claims, 6 Drawing Sheets

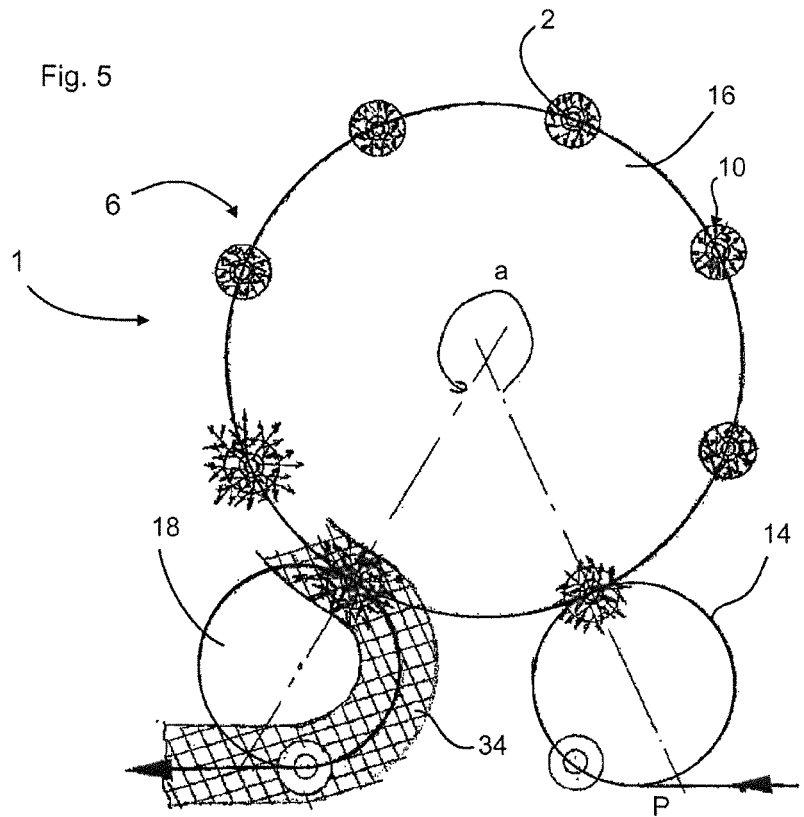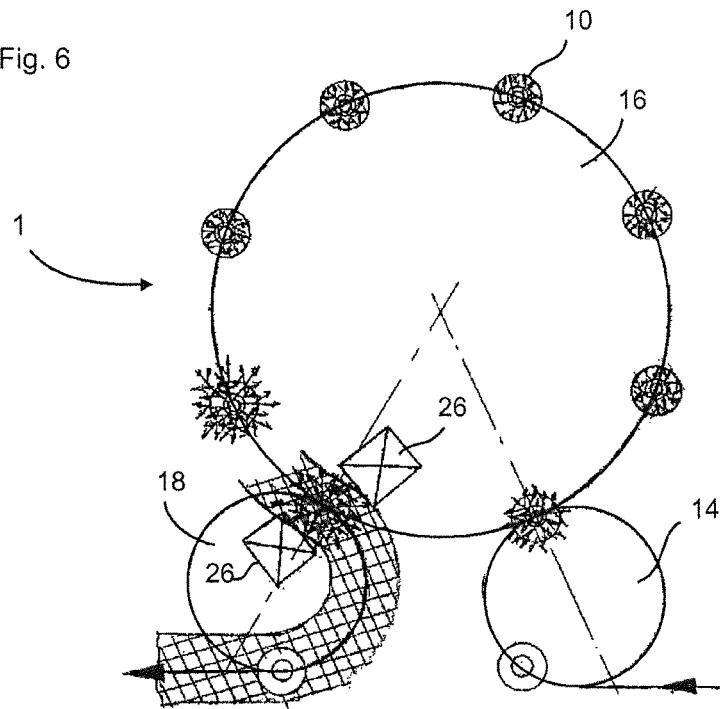

⬚ = non-sterile = dose < 25 kGy
⬚ = sterile = dose > 25 kGy

⬚ = non-sterile = dose < 25 kGy
⬚ = sterile = dose > 25 kGy

▨ = non-sterile = dose < 25 kGy
▨ = sterile = dose > 25 kGy

▨ = non-sterile = dose < 25 kGy
▨ = sterile = dose > 25 kGy

METHOD AND APPARATUS FOR THE STERILIZATION OF CONTAINERS

BACKGROUND

The present invention relates to a method and an apparatus for the sterilization of containers. In the field of the beverage production industry it is known for containers, for example plastics material containers, to be sterilized before their filling. In this case this sterilization can be carried out in widely differing ways. In this way, it is possible for example for the containers to be sterilized with a sterilization agent, such as for example $H_2O_2$ (hydrogen peroxide) or peracetic acid. The handling of these media is not without its problems, however, since they can also have harmful effects on humans. In addition, when using these media it is necessary to rinse the container afterwards.

In recent years methods have also become known in which containers are sterilized by means of charge carrier irradiation and, in particular, electron irradiation. In this way, DE 10 2008 007 428 A1 describes a method and an apparatus for the sterilization of packaging materials. In this case a treatment head for the treatment of an inner face of packaging material with electron irradiation is positioned in the respective packaging material through an aperture in the packaging material. EP 1 982 921 A1 of the Applicants describes an apparatus for the sterilization of containers. This apparatus has a treatment head with an outlet window through which charge carriers can issue. The contents of the disclosure of EP 1 982 921 A1 are hereby made the subject of the present disclosure by reference in its entirety. An apparatus for the sterilization of containers by means of charge carriers, which in particular also describes a cooling device for the outlet window for the electrons, is likewise known from DE 10 2008 025 868 A1. In addition, the contents of the disclosure of DE 10 2008 025 868 A1 are hereby also made the subject of the present application by reference.

The sterilization of the inner walls of the plastics material containers, however, is in part not sufficient for an overall sterilization.

SUMMARY

The object of the present invention is therefore to permit a sterilization of the plastics material containers in such a way that they can then be filled with a liquid and, in particular, a beverage, without a further or preceding sterilization procedure having to take place.

In a method according to the invention for the sterilization of containers the containers are conveyed along a pre-set conveying path by a conveying device. In addition, an irradiation device is introduced by a relative movement between the container and the irradiation device in a longitudinal direction of the container into the container to be sterilized and emits a charge carrier irradiation in order to sterilize the inner wall of the container by means of this charge carrier irradiation.

According to the invention an aperture region—situated on the outside—of the container is also sterilized.

In this case the region situated on the outside is understood, in particular, to be an aperture region of that container, the inner surface of which is sterilized. Furthermore, the aperture region is understood to be the region of the aperture and possibly also the adjoining head region of the container. In this way, in particular, a thread region of the container is also sterilized on the outside. It is thus advantageous for those regions of the container to be sterilized which during the subsequent filling procedure come into contact with the liquid to be poured in or with the container closure. It is preferable for the head and aperture regions of the plastics material pre-forms also to extend as far as a carrier ring optionally arranged on the containers.

The containers are preferably plastics material containers, the term "container" being understood to be both finished containers, such as for example bottles, and for example plastics material pre-forms which in particular are capable of being shaped to form plastics material containers.

It is advantageous for the aperture region situated on the outside to be sterilized by the irradiation device. It is particularly preferred for this sterilization of the aperture region situated on the outside to be carried out immediately before or immediately after the sterilization of the inner surfaces of the container. It is advantageous for the container to be a plastics material container.

In the case of a further advantageous method the sterilization of the aperture region is carried out while the irradiation device is situated completely outside the container.

In the case of a particularly preferred method the irradiation device has a rod-shaped body which is introduced into the interior of the container—in particular through the aperture. In this case an outlet window, through which electrons can issue out of the rod-shaped body, can be arranged in an end portion of this rod-shaped body.

In the case of a further advantageous method, during the sterilization of the aperture region a lower end of the irradiation device or the aforesaid end portion is situated at a distance from it which is between 0.5 cm and 10 cm, preferably between 1 cm and 6 cm and in a particularly preferred manner between 3 cm and 5 cm. On account of these specified measurements it is possible for the charge carriers, such as in particular electrons, issuing from the irradiation device still to have sufficient range to sterilize the aperture region and the head region of the container adjoining it.

In the case of a further advantageous method regions of the outer wall of the container which are situated below the aperture and head region are not sterilized by irradiation with the charge carrier irradiation. In these regions it is possible for the sterilization to be omitted since these regions cannot come into contact with the beverage to be filled.

In the case of a further advantageous method the containers are conveyed through or into a clean room. In this way it is possible for a clean room of this type to adjoin the irradiation devices directly, but it would also be possible for the irradiation to be carried out already inside a clean room and for this clean room to continue after the sterilization procedure. In the case of a further advantageous method the irradiation device irradiates the aperture region of the container at least until the container has entered a sterile room. In this case it is advantageous for a boundary of this sterile room to be capable of being defined on the other side of (for example below) the aperture region of the container described above, i.e. for example in the direction of the base of the container. In this case it is possible for the container to perform a reciprocating movement beyond the boundary of the sterile room.

In the case of a further advantageous method the container is acted upon with a directed flow of a gaseous medium. In this way for example, the container can be acted upon with sterile air which, in particular, flows in a longitudinal direction of the container. In this way, the boundary of the sterile room can also be kept or defined below the aforesaid aperture region of the container even without physical separation. It is advantageous for air filters, through which the sterile air flows, to be provided. Preferably the flow of the gaseous medium has a component which runs from a neck of the container to a bottom of the container.

In the case of a further advantageous method the irradiation takes place at least for a time, while the irradiation device is removed from a base of the container. In other words, the irradiation advantageously takes place during a withdrawal of the irradiation device out of the container. In this case it is possible for the irradiation only to start as soon as the irradiation device has been withdrawn out of the container again. It would also be possible, however, for the irradiation to take place both during the dipping and during the withdrawal of the irradiation device.

In addition, it is possible for the irradiation to take place during the entire withdrawal procedure of the irradiation device, i.e. in particular even if the end portion of the irradiation device is already situated outside the container again.

The present invention further relates to an apparatus for the sterilization of containers, the apparatus having a conveying device which conveys the containers along a pre-set conveying path, and an irradiation device which emits a charge carrier irradiation and, in particular, an electron irradiation, in which case this irradiation device is capable of being introduced by a relative movement between the container and the irradiation device in the longitudinal direction of the container into the interior of the container in order to sterilize an inner wall of the container.

According to the invention the apparatus has a control device for controlling the irradiation device, which has the effect that even an aperture region—situated on the outside—of the container is sterilized by the irradiation emitted by the irradiation device.

It is preferable for a further apparatus for the treatment of containers to be arranged downstream of the apparatus for the sterilization of the containers in the conveying direction of the containers. This further apparatus can be for example a filling device which fills the containers in particular with a liquid, such as for example a beverage. In addition, however, the further machine can also be a machine which treats plastics material pre-forms, for example a shaping device which shapes the plastics material pre-forms into plastics material containers or even a heating device which heats plastics material pre-forms.

It is thus also proposed with respect to the apparatus that the irradiation specified should also be activated while the irradiation device is situated at least in part and preferably completely outside the container.

It is advantageous for the irradiation device to have on an end face thereof an outlet window through which the charge carriers or electrons can issue out of the irradiation device.

It is advantageous for this irradiation device to move jointly with the containers at least locally along the conveying path of the latter. In this way, it is possible for a carrier device for example to be provided on which are arranged a plurality of irradiation devices, as well as also a plurality of conveying devices for conveying the containers. During this conveying of the containers the irradiation devices, which in this case have rod-like bodies for example, can thus be introduced into the interior of the containers in order to sterilize them.

In the case of a further advantageous embodiment the apparatus has an acceleration device and preferably a plurality of acceleration devices which accelerates or accelerate the electrons in the direction of the aforesaid outlet window of the irradiation device. In the case of a further advantageous embodiment the apparatus also has a stressing device in order to act upon the containers with a flow of a gaseous medium.

It is advantageous for the containers to be guided during their sterilization along at least one conveying path which is circular locally.

In the case of a further advantageous embodiment the apparatus has a sterile room through which the containers are guided. In this case it is possible for this sterile room to be designed in the form of a channel around the conveying path of the containers. In particular, it would be possible for the aforesaid sterile room to be designed in the form of a ring around the conveying path of the containers. In this way it is possible for the volume of the aforesaid sterile room to be kept relatively small in order to permit the sterile conditions to be maintained in an inexpensive manner in this way.

BRIEF DESCRIPTION OF THE DRAWINGS

Further advantages and embodiments are evident from the accompanying drawings. In the drawings

FIG. 5 is a diagrammatic illustration of a sterilization procedure with conveying of the containers;

FIG. 6 shows a further possible embodiment of a sterilization device for containers;

DETAILED DESCRIPTION

Figure 1:
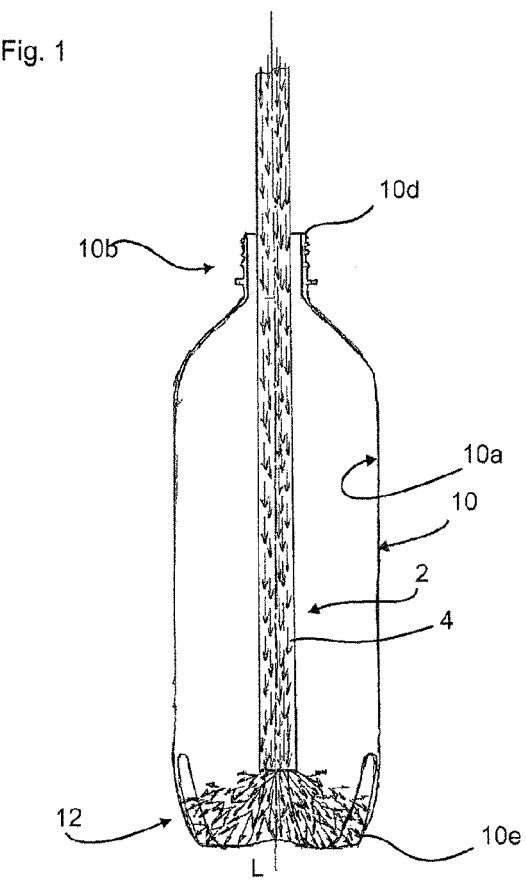
FIG. 1 is a diagrammatic illustration of a sterilization procedure.
Figure 2:
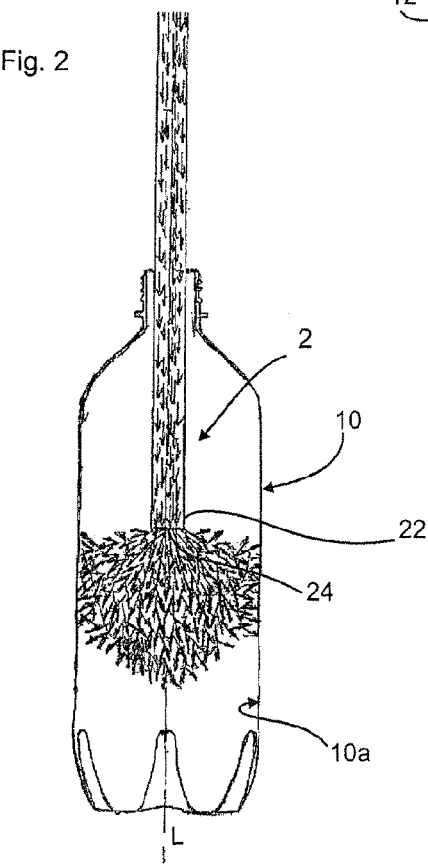
FIG. 2 is a further diagrammatic illustration of a sterilization procedure.
Figure 3:
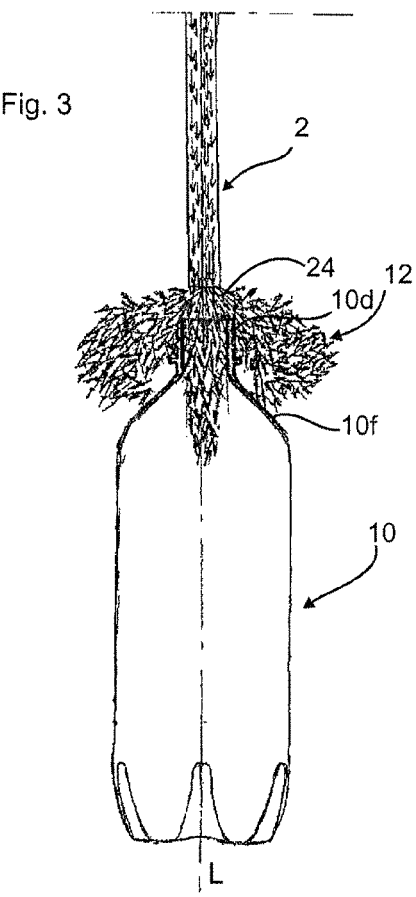
FIG. 3 is a further diagrammatic illustration of a sterilization procedure.

FIGS. 1 to 3 diagrammatically show three illustrations to demonstrate the sterilization process. In this case a sterilization device 2 (shown only diagrammatically) is provided, which is designed here in the form of a rod-shaped body which is capable of being introduced into the interior of the container 10 through an aperture 10d. In the situation shown in FIG. 1 the irradiation device is introduced into the container almost as far as the base 10e of the latter and, in this way, it can also act upon the aforesaid base region 10e with an electron cloud 12. As a result of this stressing the inner wall of the plastics material container designated 10a in its entirety is sterilized. In this case the electrons 4 are accelerated by an acceleration device (not shown). The reference 10b designates an aperture region which contains the aperture 10d and which extends, however, further (downwards) in the longitudinal direction L of the container than the aperture 10d.

FIG. 2 shows a second situation in which the lower end portion 22 is arranged with the outlet window 24 in a middle region of the container 10. In this case a middle region of the inner wall is sterilized.

It is possible in this case for the movement of the irradiation device 2 with respect to the container 10 to take place at a constant speed, but it would also be possible for the speed to be dependent for example upon a contour of the container and for a slower relative movement for example to take place with regions of larger cross-section and for a more rapid movement to take place with regions of smaller crosssection, in order to apply a radiation dosage which is constant in each case to the inner wall 10a of the container in this way.

In this case with all the arrangements the relative movement between the containers 10 and the irradiation device 2 takes place in a longitudinal direction L of the container 10.

FIG. 3 shows a further position of the irradiation device 2 with respect to the container 10. In this case the irradiation device 2 or the outlet window 24 are withdrawn completely out of the container 10. The electron cloud 12 acts upon the aperture 10*d* of the container both from the inside and from the outside, and thus effects sterilization of this aperture. In addition, however, the aperture region is also acted upon with electrons and in this case also an upper area 10*f* of the container.

Figure 4:
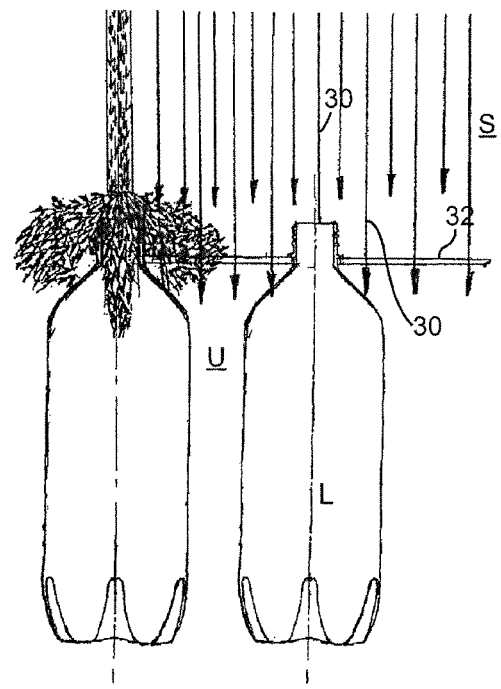
FIG. 4 is an illustration of the sterilization procedure with additional stressing by air.

FIG. 4 illustrates the situation shown in FIG. 3, in which case a directed air flow 30 is additionally directed onto the containers. More precisely, the stressing with the sterile air likewise takes place in the longitudinal direction L of the container in order to prevent a shifting of the sterile room boundary in this way. The reference letter U designates the non-sterile region and the reference letter S the sterile region. The reference number 32 designates the sterile room boundary, it being unnecessary in this case for the latter to have to be formed by a material boundary. It would also be possible, however, for the air flow to strike the plastics material containers obliquely with respect to the longitudinal direction of the latter here as well. It is preferable, however, for this air flow 30 also to have a component which extends in the longitudinal direction L—in particular from the aperture of the containers to the base of the containers.

FIG. 5 is a rough diagrammatic illustration of an apparatus 1 according to the invention. In this case the apparatus 1 has a carrier wheel 16 on which a plurality of conveying elements (not shown) for holding the containers 10 are arranged. This carrier wheel is thus part of a conveying device 6 for conveying containers. In addition, a plurality of irradiation devices 2, which can be introduced into the apertures of the plastics material containers as in the manner shown above, are arranged on this carrier wheel 16. The reference letter P designates the conveying path of the containers and the reference letter a designates the treatment angle for the sterilization. First of all non-sterile containers 10 are delivered to the carrier wheel 16 by way of an infeed wheel 14. During the conveying with the carrier wheel 16 the plastics material containers are first sterilized on their inner wall. When the containers run out or when they are transferred to the run-out wheel 18 they are also sterilized in their aperture region and thus also on the outside.

The reference number 34 designates a sterile room into which the containers pass while they are still being sterilized. After that, the now sterile containers are conveyed out through the sterile room 34 which is in the form of a channel here. In this region of the sterile room it is also possible, as mentioned above, for a sterile zone to be formed only above a specified region of the containers, for example above a neck ring, but not below it.

FIG. 6 shows a further embodiment of an apparatus according to the invention. In contrast to the embodiment shown in FIG. 5, in this case an additional sterilization device 26 is provided which sterilizes the aperture region of the plastics material containers, in this case in particular likewise by stressing with electrons. In addition, however, other procedures for sterilization would also be possible in this case, for example sterilization with UV radiation or with X-ray radiation, with gamma radiation and the like. This sterilization device 26 is arranged in a stationary manner in this case.

Figure 7:
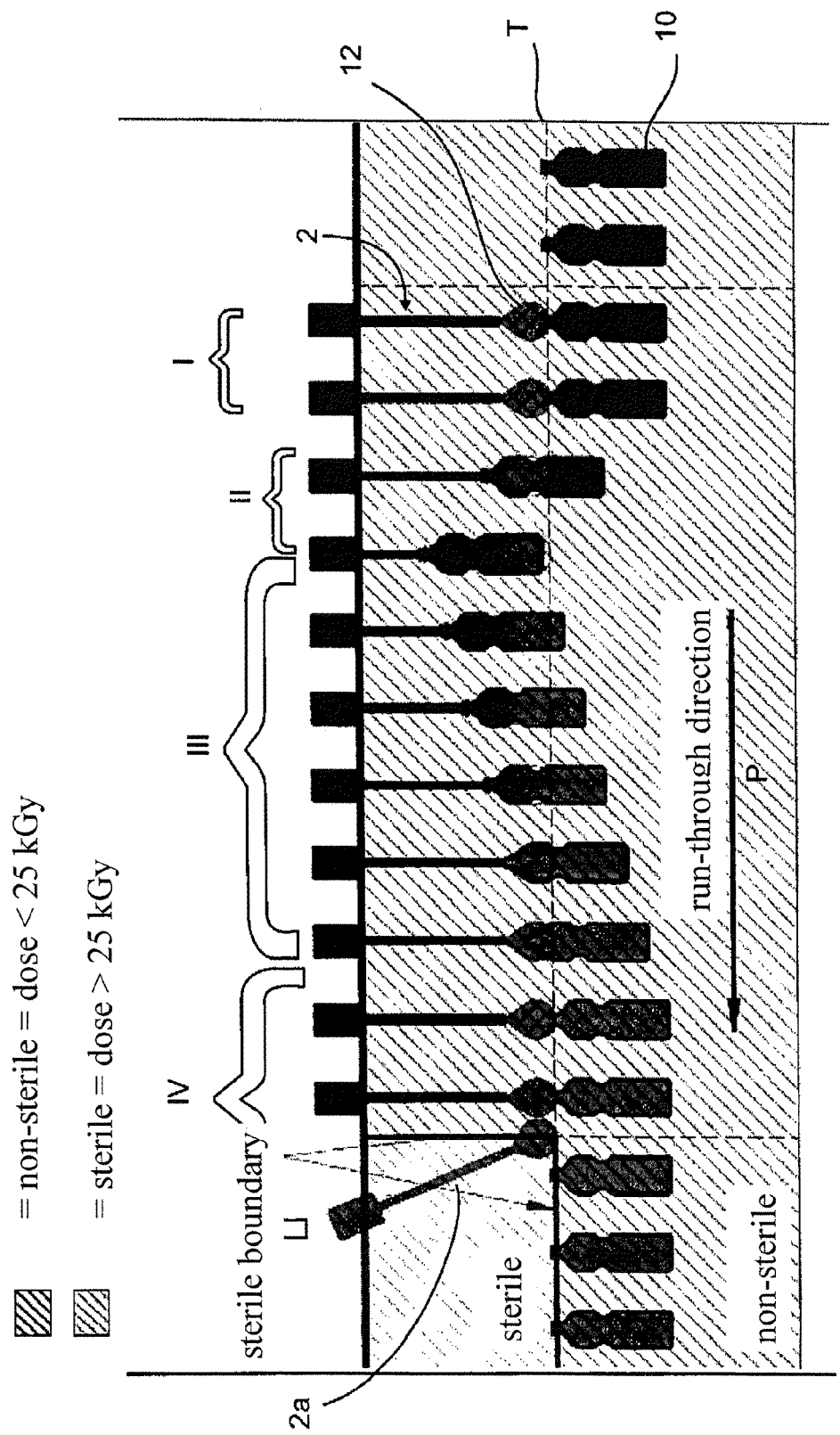
FIG. 7 is a diagrammatic illustration of a sterilization sequence.

FIG. 7 is a further illustration to show the sterilization procedure. In this case a plurality of irradiation devices 2 are provided, which in this case are conveyed jointly with the containers 10 along the conveying path P. This conveying path P, as already mentioned above, can be both circular and straight or can have other directions of movement. It is evident in this case that the individual irradiation devices 2 are designed to be fixed, i.e. they do not move in the longitudinal direction of the containers. It is rather that the containers are raised here, so that the irradiation devices 2 penetrate into the interior of the containers, so that sterilization can take place here.

The broken line T in this case designates a separation line between a sterile region and a non-sterile region. A radiation dose which is above 25 kGy can be applied in the sterile region and the dose is accordingly below 25 kGy in the non-sterile region. In this case the sterilization process can be divided into a number of portions I-IV. In portion I the containers are not raised or lowered along their longitudinal direction, and in this region the apertures of the containers are acted upon with the electron cloud 12, so that sterilization takes place here. In region II the containers are raised up, so that the irradiation device 2 penetrates into the interior of the containers. In this way, sterilization of the base region and also a middle region of the container is possible.

In portion III the containers are then lowered again, in which case a sterilization of the inner surface of the containers also takes place in this portion, as shown in FIG. 7. In the two right-hand states of portion III, however, an irradiation of the outer aperture region of the container also takes place with the container already almost lowered again. It is evident that the containers are raised more rapidly than they are then lowered again. It is therefore preferable for the irradiation device 2 to be introduced into the containers more rapidly than it is then removed from them again.

In portion IV the containers are again conveyed in their lower position and are irradiated in their aperture region. In this case it is also possible for an irradiation device 2*a* to be provided, which is orientated obliquely or is arranged generally in another manner, and the containers are irradiated from the side. In addition, it would also be possible for the plastics material containers also to be rotated about their longitudinal axis during the internal irradiation so as to achieve a still more uniform distribution of the electrons on the inner surface of the containers in this way.

Figure 8A:
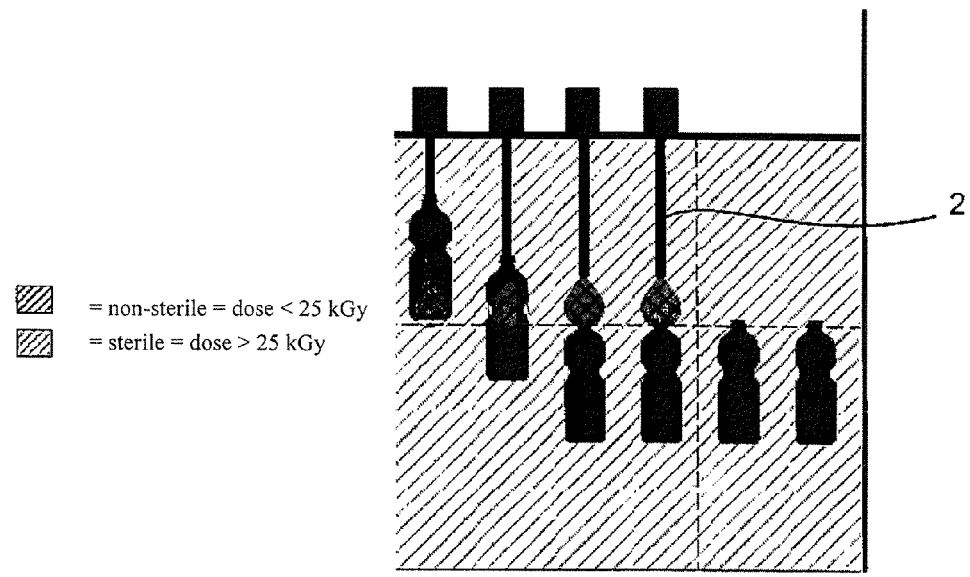
FIGS. 8a to 8d are four detailed illustrations of the sterilization sequence shown in FIG. 7.
Figure 8B:
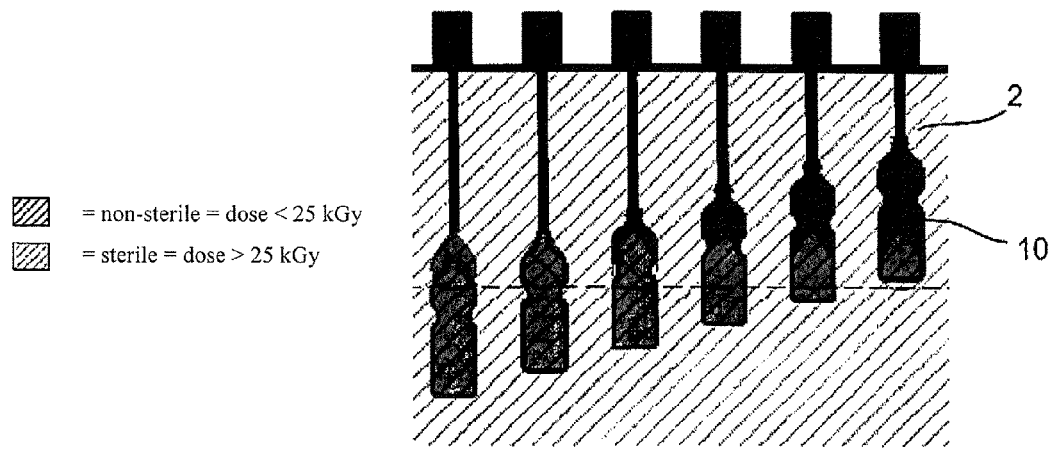

FIGS. 8*a* to 8*b* show the individual portions in a more detailed illustration. In this case it would be possible in the situation shown in FIG. 8*a* for the containers to run in by way of a sluice wheel for example, in which case it is preferable for the existing gamma radiation to be screened off. In addition, the containers are raised above the electron irradiation device 2 in this case, it being preferable for no disinfection of the inner surface to take place at first. This begins only in the two situations shown on the left in FIG. 8*b*.

In the situation shown in FIG. 8*b* the container is lowered successively with respect to the irradiation device 2 and during this time a minimum dosage is also applied to the inner surface of the container. In this case the occurrence of arcs (breaks of the electron irradiation) is critical. When arcs occur the dosage on the surface of the inside of the container is too low. In the event that such an occurrence of an arc is ascertained, in particular by means of sensor devices, it is possible for the containers not to be transferred into the following sterile region but to be treated once again or separated out. The treatment duration required for the electron irradiation dosage can be regulated by way of the lowering or raising speed of the containers. The boundaries of a permissible dosage necessitate an adapted movement profile for lowering the containers and the necessary dipping depth.

For raising and lowering the containers, use can be made for example of drives such as mechanical lifting cams. In addition, it would also be possible for linear motors, electric motors, hydraulic drives or pneumatic drives to be used in order to lift the containers. Conversely, however, it would also be possible to raise or lower not the containers themselves but instead of this (or in addition) the individual irradiation devices 2.

As is evident from FIG. 8b, disinfection of the outside of the containers does not take place, so that by definition the region outside the container is non-sterile. In the situation shown in FIG. 8c the container is situated below the irradiation device 2. Here at least a minimum dosage is applied to the outside of the container or receptacle.

When the irradiation device dips into the containers it is not absolutely necessary for a sterilization action to take place. In this case the irradiation can be turned on or also off here. According to the definition of sterilization it is possible for recontamination to occur again above the outlet window at which the radiation cloud 12 is present, for example as a result of the fact that, as above, germs are introduced through the aperture. Nevertheless, however, irradiation downwards from above affords an additional degree of safety, as shown in FIG. 8a.

The actual sterilization begins, as shown in FIG. 8b, from the base of the container in the interior of the container by relative movements of the irradiation device in the direction of the aperture of the container. In this case, as mentioned above, this relative movement of the container wall can be adapted for example to a wall thickness or even a wall diameter. It is advantageous for any exchange of gas inside the container, which occurs between the sterile region and the non-sterile region during the disinfection in the container, to have the result that all these regions have to move through the radiation cloud 12 and thus be sterilized, as shown in FIG. 8b.

In the third step the irradiation device is pulled out of the container and is positioned or moved above the aperture in such a way that the aperture is sterilized in the outer region preferably as far as the carrier ring and, in particular, the opening of the aperture is irradiated at the same time in such a way that all the particles which drop into the containers have to pass in turn through the sterilizing cloud 12. As a result of this protection in the radiation cloud the sterilization can take place in a non-sterile environment and can also be maintained.

Figure 8C:
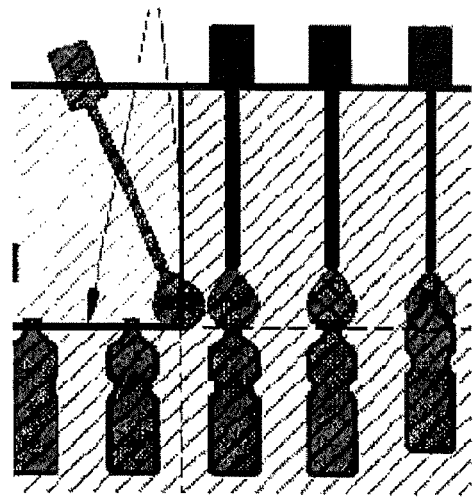

FIG. 8c shows this maintenance of the sterilization state. In this case too, the issue of micro-organisms is prevented in the case of a previous arc during the disinfection of the inside of the bottle. As above, in this case too the occurrence of arc indicates an excessively low dosage on the neck ring. The container is not transferred into the sterile region, but is treated once again or is separated out.

Furthermore, it is preferable for the treatment duration for the minimum dosage or the duration of the residence time in the electron beam to be regulated in such a way that an overdosage of other surfaces is prevented.

Figure 8D:
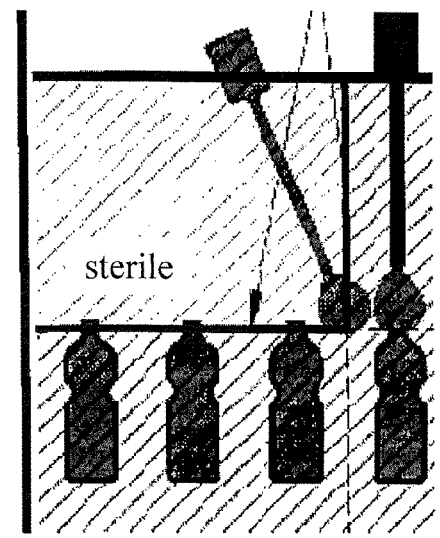

FIG. 8d shows a further step of the disinfection of the container. Here the container is sterilized on the inside and also in the aperture region and it is protected from recontamination by the radiation cloud 12 which is nevertheless still applied. After that, the container is transferred into a sterile room which extends only in the region of the aperture of the container. Neck ring insulating means of this type are known in the prior art, where merely a small area, which is present only around and above the aperture, is sterile in these sterilizing means. As mentioned above, use can be made in this case of a directed movement of sterile air, preferably downwards from above, in order to ensure the sterility.

Additional means can be used, such as for example radiation emitters, air nozzles, UV lamps or plasma, for the transfer from the radiation cloud into the sterile air flow.

After the sterilization procedure the containers can be transferred to a sluice wheel or a transfer star wheel at the outlet. In this case it is preferable for the arcs of the rotating emitters to be protected by static emitters during the treatment of the interior and the neck. The protection of the sterile zone from contamination is likewise preferably carried out—in particular by an irradiation device.

A minimum dosage on the outside of the container can, as mentioned above, also be implemented by static emitters.

With respect to the arcs, however, static emitters are critical in part, in particular if an arc has already occurred on a rotating emitter during the treatment on the inside or in the aperture region.

At the outlet the containers can be removed in turn by way of a sluice wheel, in which case screening of the gamma radiation also takes place in turn here.

The conveying device for conveying the containers can convey the containers for example on their bases, but it would also be possible for the conveying device to convey the containers on their apertures or on their carrier ring. In addition, conveying by way of the side walls of the containers would also be possible.

Within the scope of an after-treatment the containers can also be rinsed with sterile air. In this case for example, ozone which has been produced during the treatment can be blown out.

The Applicants reserve the right to claim all the features disclosed in the application documents as being essential to the invention, insofar as they are novel either individually or in combination as compared with the prior art.

What is claimed:

1. A method of sterilizing containers, comprising:
conveying a container having an open end with an aperture along a pre-set conveying path by a conveying device;
inserting an irradiation device into an interior of the container;
sterilizing the container by emitting a charge carrier irradiation beginning at a base of the container in the interior of the container and moving the irradiation device relative to an inner wall of the container in a direction of the aperture to sterilize an inner wall of the container in its entirety by means of said charge carrier irradiation and sterilizing an aperture region situated on the outside of the container as the irradiation device moves out of the aperture,
wherein the container is in an upright position and the open end of the container is facing upward during both the sterilization of the container and the aperture region.

2. The method according to claim 1, wherein sterilizing the aperture region is carried out while the irradiation device is situated completely outside the container.

3. The method according to claim 2, wherein during the sterilization of the aperture region, a lower end of the irradiation device is situated at a distance which is between 0.5 cm and 10 cm, preferably between 1 cm and 6 cm and in a particularly preferred manner between 3 cm and 5 cm.

4. The method according to claim 1, wherein regions of the outer wall of the container which are situated below the aperture and head region are not sterilized by irradiation with the charge carrier irradiation.

5. The method according to claim 1, wherein the containers are conveyed through or into a clean room.

6. The method according to claim 1, wherein the irradiation device irradiates the aperture region of the container at least until the container has entered a sterile room.

7. The method according to claim 1, wherein the container is acted upon with a directed flow of a gaseous medium.

8. The method according to claim 7, wherein the gaseous medium is sterile air.

9. The method according to claim 7, wherein the gaseous medium flows in a longitudinal direction of the container.

10. The method according to claim 7, wherein the flow of the gaseous medium has a component which runs from the neck of the container to the bottom of the container.

11. The method according to claim 10, wherein during sterilization of the aperture region a lower end of the irradiation device is situated at a distance from the aperture which is between 1 cm and 6 cm.

12. The method according to claim 10, wherein during sterilization of the aperture region a lower end of the irradiation device is situated at a distance from the aperture which is between 3 cm and 5 cm.

13. The method according to claim 1, wherein the irradiation takes place while the irradiation device is removed from a base of the container.

14. The method according to claim 1, wherein the irradiation device also acts upon a base region of the container with an electron cloud.

15. The method according to claim 1, wherein an electron cloud acts upon the aperture of the container both from the inside and from the outside of the container.

16. The method according to claim 1, wherein the charge carrier irradiation includes electrons accelerated by an acceleration device.

17. The method according to claim 1, wherein during sterilization of the aperture region a lower end of the irradiation device is situated at a distance from the aperture which is between 0.5 cm and 10 cm.

18. The method of claim 1, further comprising controlling the duration of the sterilization of the container and the aperture region by controlling the lowering or raising speed of the container.

19. The method of claim 1, further comprising moving the irradiation device at different speeds within the container to account for different cross-sectional shapes.

20. A method of sterilizing containers, comprising:

conveying a container having a vertical longitudinal axis, and an open end with an aperture along a pre-set conveying path by a conveying device;

inserting a first irradiation device into an interior of the container;

sterilizing the container by emitting a charge carrier irradiation beginning at a base of the container in the interior of the container and moving the irradiation device relative to an inner wall of the container in a direction of the aperture to sterilize an inner wall of the container in its entirety by means of said charge carrier irradiation and sterilizing an aperture region situated on the outside of the container as the irradiation device moves out of the aperture;

orienting a second irradiation device obliquely to said vertical longitudinal axis of the container and irradiating the container on a side of the container, wherein the container is in an upright position and the open end of the container is facing upward during both the sterilization of the container and the aperture region.

21. A method of sterilizing containers, comprising:

conveying a container having an open end with an aperture along a pre-set conveying path by a conveying device, wherein the container is a plastic preform;

inserting an irradiation device into an interior of the container;

sterilizing the container by emitting a charge carrier irradiation beginning at a base of the container in the interior of the container and moving the irradiation device relative to an inner wall of the container in a direction of the aperture to sterilize an inner wall of the container in its entirety by means of said charge carrier irradiation and sterilizing an aperture region situated on the outside of the container as the irradiation device moves out of the aperture, wherein the container is in an upright position and the open end of the container is facing upward during both the sterilization of the container and the aperture region.

\* \* \* \* \*